US012086979B2

(12) United States Patent
Prokop et al.

(10) Patent No.: US 12,086,979 B2
(45) Date of Patent: Sep. 10, 2024

(54) MULTI-PHASE FILTER

(71) Applicants: Stichting Radboud universitair medisch centrum, Nijmegen (NL); CANON MEDICAL SYSTEMS CORPORATION, Otawara (JP)

(72) Inventors: Mathias Prokop, Nijmegen (NL); Brian Mohr, Edinburgh (GB); Paul Thomson, Edinburgh (GB); Ewan Hemingway, Edinburgh (GB)

(73) Assignees: Stichting Radboud universitair medisch centrum, Nijmegen (NL); CANON MEDICAL SYSTEMS CORPORATION, Otawara (JP)

( * ) Notice: Subject to any disclaimer, the term of this patent is extended or adjusted under 35 U.S.C. 154(b) by 188 days.

(21) Appl. No.: 17/128,430

(22) Filed: Dec. 21, 2020

(65) Prior Publication Data

US 2022/0198651 A1    Jun. 23, 2022

(51) Int. Cl.
   *G06T 7/00* (2017.01)
(52) U.S. Cl.
   CPC .. *G06T 7/0012* (2013.01); *G06T 2207/20032* (2013.01); *G06T 2207/20081* (2013.01)
(58) Field of Classification Search
   CPC ......... G06T 7/0012; G06T 2207/20032; G06T 2207/10081; G06T 7/90; G06T 5/002;
   (Continued)

(56) References Cited

U.S. PATENT DOCUMENTS 7,974,473 B2    7/2011  Nanbu
9,111,337 B2    8/2015  Ramirez Giraldo et al.
(Continued)

FOREIGN PATENT DOCUMENTS

EP    3244368 A1 * 11/2017  ............ G06T 5/002
JP    2011-092547 A    5/2011
(Continued)

OTHER PUBLICATIONS

Van De Leemput, S. C., Meijs, M., Patel, A., Meijer, F. J. A., Van Ginneken, B., & Manniesing, R. (2019). Multiclass Brain Tissue Segmentation in 4D CT Using Convolutional Neural Networks. In IEEE Access (vol. 7, pp. 51557-51569). Institute of Electrical and Electronics Engineers (IEEE). (Year: 2019).*

(Continued)

*Primary Examiner* — Aaron W Carter
*Assistant Examiner* — Courtney Joan Nelson
(74) *Attorney, Agent, or Firm* — Oblon, McClelland, Maier & Neustadt, L.L.P.

(57) ABSTRACT

An apparatus including processing circuitry configured to: acquire a plurality of sets of medical imaging data of a region of a subject, each set of data corresponding to a respective different measurement period; apply a filter to the plurality of medical imaging data sets to produce a plurality of filtered medical imaging data sets corresponding to the different measurement periods, wherein the applying of the filter is such that, for each of the medical imaging data sets, the filtering uses at least some information from the other medical imaging data sets acquired at the different time periods and wherein the applying of the filter comprises applying at least one constraint or condition and the constraint or condition comprises preserving at least one measure of intensity for each medical imaging data set.

22 Claims, 7 Drawing Sheets

(58) Field of Classification Search
CPC . G06T 2207/20216; G06T 2207/30004; G06T 2207/10024; G06T 2207/10076; G06T 3/4007; G06T 5/10; G06T 2207/20081; A61B 6/032; A61B 8/5223; A61B 5/1032; A61B 6/5217; A61B 8/13; A61B 8/463; A61B 6/03; A61B 5/0013; G16H 30/40; G06V 10/56; G06V 2201/03
See application file for complete search history.

(56) References Cited

U.S. PATENT DOCUMENTS

| | | | |
|---|---|---|---|
| 9,585,636 | B2 | 3/2017 | Osumi et al. |
| 2009/0002369 | A1* | 1/2009 | Rottger .................. G06T 15/08 345/424 |
| 2009/0285461 | A1 | 11/2009 | Bohm et al. |
| 2010/0128841 | A1 | 5/2010 | Imas et al. |
| 2011/0026797 | A1 | 2/2011 | Declerck et al. |
| 2011/0268328 | A1 | 11/2011 | Bar-Aviv et al. |
| 2017/0154413 | A1* | 6/2017 | Yu ....................... G06F 18/2135 |
| 2017/0337682 | A1 | 11/2017 | Liao et al. |
| 2017/0372474 | A1 | 12/2017 | Behar et al. |
| 2018/0165819 | A1 | 6/2018 | Carolus et al. |
| 2018/0214133 | A1 | 8/2018 | Mine et al. |
| 2018/0315225 | A1* | 11/2018 | Zhang .................. G06T 7/0012 |
| 2019/0180419 | A1 | 6/2019 | Smit et al. |
| 2019/0180500 | A1 | 6/2019 | Shen et al. |
| 2019/0213715 | A1 | 7/2019 | Li et al. |
| 2019/0350538 | A1* | 11/2019 | Wilson ................... G06T 5/001 |

FOREIGN PATENT DOCUMENTS

| | | |
|---|---|---|
| JP | 4820582 B2 | 11/2011 |
| WO | WO 2008/122056 A2 | 10/2008 |
| WO | WO 2010/073251 A2 | 7/2010 |

OTHER PUBLICATIONS

K. Suzuki, I. Horiba and N. Sugie, "Efficient approximation of neural filters for removing quantum noise from images," in IEEE Transactions on Signal Processing, vol. 50, No. 7, pp. 1787-1799, Jul. 2002, doi: 10.1109/TSP.2002.1011218. (Year: 2002).*

Van De Leemput et al., "Multiclass Brain Tissue Segmentation in 4D CT Using Convolutional Neural Networks", IEEE Access, vol. 7, 2019, pp. 51557-51569, XP011721673.

Extended European Search Report issued May 19, 2022 in European Patent Application No. 21214737.5, 9 pages.

He et al., "Guided Image Filtering", IEEE Transactions on Pattern Analysis and Machine Intelligence, vol. 35, issue 6, Jun. 2013, 14 pages.

Singh et al., "Anisotropic Diffusion for Details Enhancement in Multiexposure Image Fusion", ISRN Signal Processing, vol. 2013, 2013, 19 pages.

Prasath, "Weighted Laplacian Differences Based Multispectral Anisotropic Diffusion", IGARSS, 2011, pp. 4042-4045.

Sanchez-Ortiz et al., "Knowledge-Based Anisotropic Diffusion of Vector-Valued 4-Dimensional Cardiac MR Images", Medical Image Analysis, vol. 3, issued 1, Mar. 1999, 10 pages.

* cited by examiner

MULTI-PHASE FILTER

FIELD

Embodiments described herein relate generally to a medical imaging method and apparatus, for example, a method and apparatus for filtering a plurality of medical imaging data sets corresponding to respective different measurement periods.

Backgrounds Medical imaging processes that involve multiple scans of a patient or scanning volume at multiple time periods (multi-phase scans) may provide clinical advantages. For example, additional information, for example, functional information may be able to be obtained from performing scans at multiple times. However, dose consideration for such scans, in particular for multi-phase CT scans, may be currently limiting widespread adoption of such multi-phase scans.

It is known that subtraction scanning processes are not widely adopted in routine clinical practice due to dose consideration. Related issues may apply to other types of multi-phase scans, for example, tri-phase liver and follow-up scanning processes.

BRIEF DESCRIPTION OF THE DRAWINGS

Embodiments are now described, by way of non-limiting example, and are illustrated in the following figures, in which.

DETAILED DESCRIPTION

Figure 1:
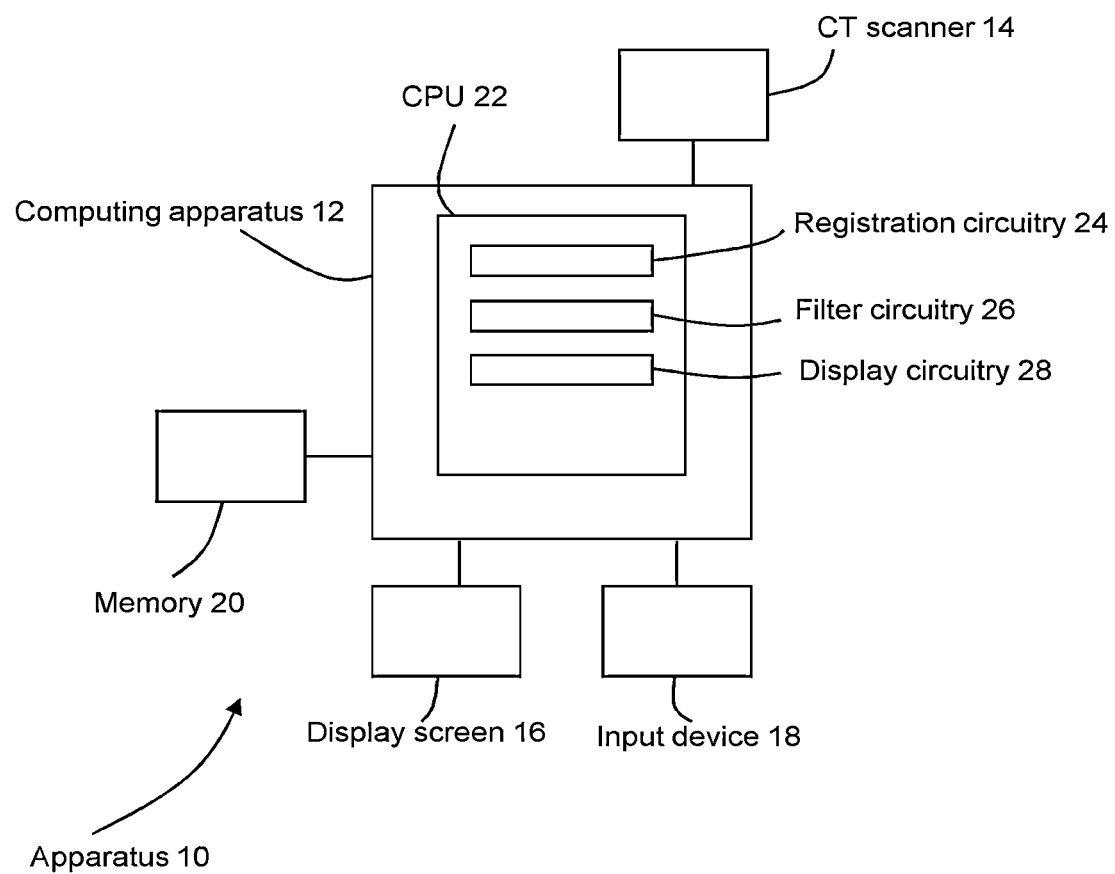
FIG. 1 is a schematic illustration of an apparatus in accordance with an embodiment.

Certain embodiments provide a medical imaging method comprising: acquiring a plurality of sets of medical imaging data of a region of a subject, each set of data corresponding to a respective different measurement period; applying a filter to the plurality of medical imaging data sets to produce a plurality of filtered medical imaging data sets corresponding to the different measurement periods, wherein the applying of the filter is such that, for each of the medical imaging data sets, the filtering uses at least some information from the other medical imaging data sets acquired at the different time periods and wherein the applying of the filter comprises applying at least one constraint or condition and the constraint or condition comprises preserving at least one measure of intensity for each medical imaging data set.

Certain embodiments provide an apparatus comprising processing circuitry configured to: acquire a plurality of sets of medical imaging data of a region of a subject, each set of data corresponding to a respective different measurement period; apply a filter to the plurality of medical imaging data sets to produce a plurality of filtered medical imaging data sets corresponding to the different measurement periods, wherein the applying of the filter is such that, for each of the medical imaging data sets, the filtering uses at least some information from the other medical imaging data sets acquired at the different time periods and wherein the applying of the filter comprises applying at least one constraint or condition and the constraint or condition comprises preserving at least one measure of intensity for each medical imaging data set.

Certain embodiments provide a system comprising processing circuitry configure to train a filter for filtering medical images, wherein the filter is characterized by one or more filter parameters, the method comprising: obtaining a plurality of sets of medical image training data of a region of a subject; performing a machine learning process on the plurality of sets of medical image training data to determine values for the one or more filter parameters thereby to obtain a trained filter, wherein the trained filter is such that filtering a plurality of sets of medical imaging data of a region of a subject, each set of data corresponding to a respective different measurement period, using the trained filter, uses at least some information from the other medical imaging data sets acquired at the different time periods and comprises applying at least one constraint or condition and the constraint or condition comprises preserving at least one measure of intensity for each medical imaging data set.

Certain embodiments provide a method for training a filter for filtering medical images, wherein the filter is characterized by one or more filter parameters, the method comprising: obtaining a plurality of sets of medical image training data of a region of a subject; performing a machine learning process on the plurality of sets of medical image training data to determine values for the one or more filter parameters thereby to obtain a trained filter, wherein the trained filter is such that filtering a plurality of sets of medical imaging data of a region of a subject, each set of data corresponding to a respective different measurement period, using the trained filter, uses at least some information from the other medical imaging data sets acquired at the different time periods and comprises applying at least one constraint or condition and the constraint or condition comprises preserving at least one measure of intensity for each medical imaging data set.

Certain embodiments provide a computer program product comprising computer-readable instructions that are executable to: acquire a plurality of sets of medical imaging data of a region of a subject, each set of data corresponding to a respective different measurement period; apply a filter to the plurality of medical imaging data sets to produce a plurality of filtered medical imaging data sets corresponding to the different measurement periods, wherein the applying of the filter is such that, for each of the medical imaging data sets, the filtering uses at least some information from the other medical imaging data sets acquired at the different time periods and wherein the applying of the filter comprises applying at least one constraint or condition and the constraint or condition comprises preserving at least one measure of intensity for each medical imaging data set.

In the following description of embodiments, a constraint or condition that comprises preserving at least one measure of intensity for each medical imaging data set is described. It will be understood that the nature of the constraint/condition and the measure of intensity may vary for different types of medical scan.

For example, as described in the following, for CT scans, a constraint or condition that comprises preserving at least one measure of density for each medical imaging data set can be used. In the following description of CT scan embodiments, the term density is used in place of the term intensity, such that the applied condition or constraint comprises preserving at least one measure of density.

It will be understood that, in general, the term intensity may relate to the strength of a detected signal during a medical scanning process, for example, a magnitude of the signal for a particular area/volume. For embodiments relating to CT scans, the density, also referred to as radio density, of a scanned tissue is proportional to the attenuation of x-ray that pass through the tissue. For example, density may be measured in Hounsfield Units or other appropriate units.

It will be understood that intensity (or density) may be measured over a group of voxels, for example, over a local region of the scan data or globally over the region of the scan data. Furthermore, in further embodiments, for scans in which contrast is used for one phase, the method may act such that substantially no contrast information is transferred between phases.

For other types of scan, the constraint may be applied to a measure of intensity of a measured signal or a quantity derived from the scan data itself. As a non-limiting example, the intensity of the scan data may be proportional to, for example, the level of a signal reflected, transmitted, attenuated or scattered during the scan. As a further non-limiting example, the intensity may be derived from the scan data itself, for example, a measure of intensity may be determined from a region of an obtained image/volume, and for example, a sub-region of an image may have a particular value of intensity. In some contexts, intensity may refer to a property of the image data itself (for example, related to brightness or darkness of the image).

An apparatus 10 according to an embodiment is illustrated schematically in FIG. 1. The apparatus 10 is configured to acquire a plurality of medical imaging data sets, in this case a plurality of computer tomography (CT) data sets, and to process the acquired plurality of imaging data sets to obtain a plurality of filtered images.

The apparatus 10 comprises a computing apparatus 12, in this case a personal computer (PC) or workstation, which is connected to a computed tomography (CT) scanner 14, one or more display screens 16 and an input device or devices 18, such as a computer keyboard, mouse or trackball. In other embodiments, the computing apparatus 12 may not be connected to the CT scanner 14.

The CT scanner 14 may be any CT scanner that is configured to obtain volumetric medical imaging data that is representative of at least one anatomical feature of a patient or other subject. The anatomical feature may be a shoulder or a different joint, for example the hip, knee or elbow. In further embodiments, the volumetric imaging data may be representative of any anatomical feature or features. For example, the volumetric imaging data may be representative of any appropriate bone or organ.

In alternative embodiments, the CT scanner 14 may be replaced or supplemented by a scanner configured to obtain imaging data in any other imaging modality, for example a cone-beam CT scanner, MRI (magnetic resonance imaging) scanner, X-ray scanner, ultrasound scanner, PET scanner (positron emission tomography) or SPECT (single photon emission computed tomography) scanner. In the present embodiment, the imaging data is three-dimensional acquired over multiple time periods. When considered collectively, the plurality of data sets may be considered as four-dimensional data. In some embodiments, three-dimensional imaging data may be obtained by acquiring multiple two-dimensional scans. In further embodiments, the method may be applied to a one-dimensional signal.

In the present embodiment, volumetric imaging data sets obtained by the CT scanner 14 are stored in memory 20 and subsequently provided to computing apparatus 12. In an alternative embodiment, volumetric imaging data sets are supplied from a remote data store (not shown) which may form part of a Picture Archiving and Communication System (PACS). The memory 20 or remote data store may comprise any suitable form of memory storage.

Computing apparatus 12 provides a processing resource for automatically processing or semi-automatically processing imaging data sets and comprises a central processing unit (CPU) 22.

The computing apparatus 12 includes registration circuitry 24 configured to perform a spatial registration process on the volumetric medical imaging data sets, for example, using a reference anatomical data set; filter circuitry 26 configured to apply a filter to the medical imaging data sets; and display circuitry 28 configured to display a selected image on display 16.

In the present embodiment, the registration circuitry 24 performs a registration process. Any known suitable registration methods may be used. As a non-limiting example, the registration process includes detecting a plurality of landmarks in the set of imaging data. Anatomical landmarks may be recognizable points within the body's structure, for example well defined points on bones, organs or other anatomical structures.

The filter circuitry 26 is configured to receive a plurality of imaging data sets, each imaging data set acquired at a respective different periods, and apply a filter to the plurality of imaging data sets to output a plurality of filtered imaging data sets.

In the present embodiment, the circuitries 24, 26 and 28 are each implemented in computing apparatus 12 by means of a computer program having computer-readable instructions that are executable to perform the method of the embodiment. However, in other embodiments, the various circuitries may be implemented as one or more ASICs (application specific integrated circuits) or FPGAs (field programmable gate arrays).

The computing apparatus 12 also includes a hard drive and other components of a PC including RAM, ROM, a data bus, an operating system including various device drivers, and hardware devices including a graphics card. Such components are not shown in FIG. 1 for clarity.

In accordance with embodiments, a method of filtering a plurality of medical imaging data sets is described. By way of background, generally when edge aware filtering is performed on an imaging data set, the edges are estimated from the data set that is being filtered (smoothed). A well-known filter, a Gaussian filter is not edge aware and smooths in all directions equally. On the other hand, an anisotropic diffusion filter is edge aware and recognizes strong gradients in the underlying intensity (for example, density for CT scan data) and does not smooth in the direction of strong gradients to preserve edges. Gradient can be understood as a difference between intensity (for example, density) levels between voxels. For example, if a first voxel has a high intensity and a second voxel has a low intensity, then there will be a strong intensity gradient between the two voxels that is indicative of a vessel boundary or edge. As a further example, if a first voxel has a first intensity and a second voxel has a similar, second intensity then there will be a smaller gradient between the two voxels.

In anisotropic diffusion filters, edges are computed or estimated using a determined intensity gradient guide or map. In certain applications, for example, in scans without contrast enhancement, certain structures may not be visible. In such scans, the edges will not be well defined and therefore, a naive application of anisotropic smoothing would lead to blending of unrelated tissue and structure. Even in cases where edges are well defined, additional noise due to the scanning process, for example due to a subtraction process, could lead to a higher error. A method, in accordance with the following embodiments, may provide an improved filtering process.

In the following, a filtering method is described, in accordance with embodiments, in which at least some information is shared between different phases of a scanning process. This information is used when filtering each set of medical imaging data from each phase separately. The combined data provides less noise and better edge definition. For example, scan data with contrast enhancement will provided definition of boundaries that may be less visible in non-contrast data. In general, the shared information indicates or informs the filtering process on where the smoothing should be performed. In known methods, if only information from the present scan was used, for example, in a pre-contrast scan, then the filtering method could end up smoothing over a vessel boundary, as the edge information from the pre-contrast scan is incomplete or less defined. In some embodiments, the at least some information comprises or is comprised in a further function or mapping, for example, a guide function, for the filter. In some embodiments, the further function or mapping is representative or at least indicative of at least one of: the anisotropy and/or features and/or edges of the volume being scanned.

Figure 2:
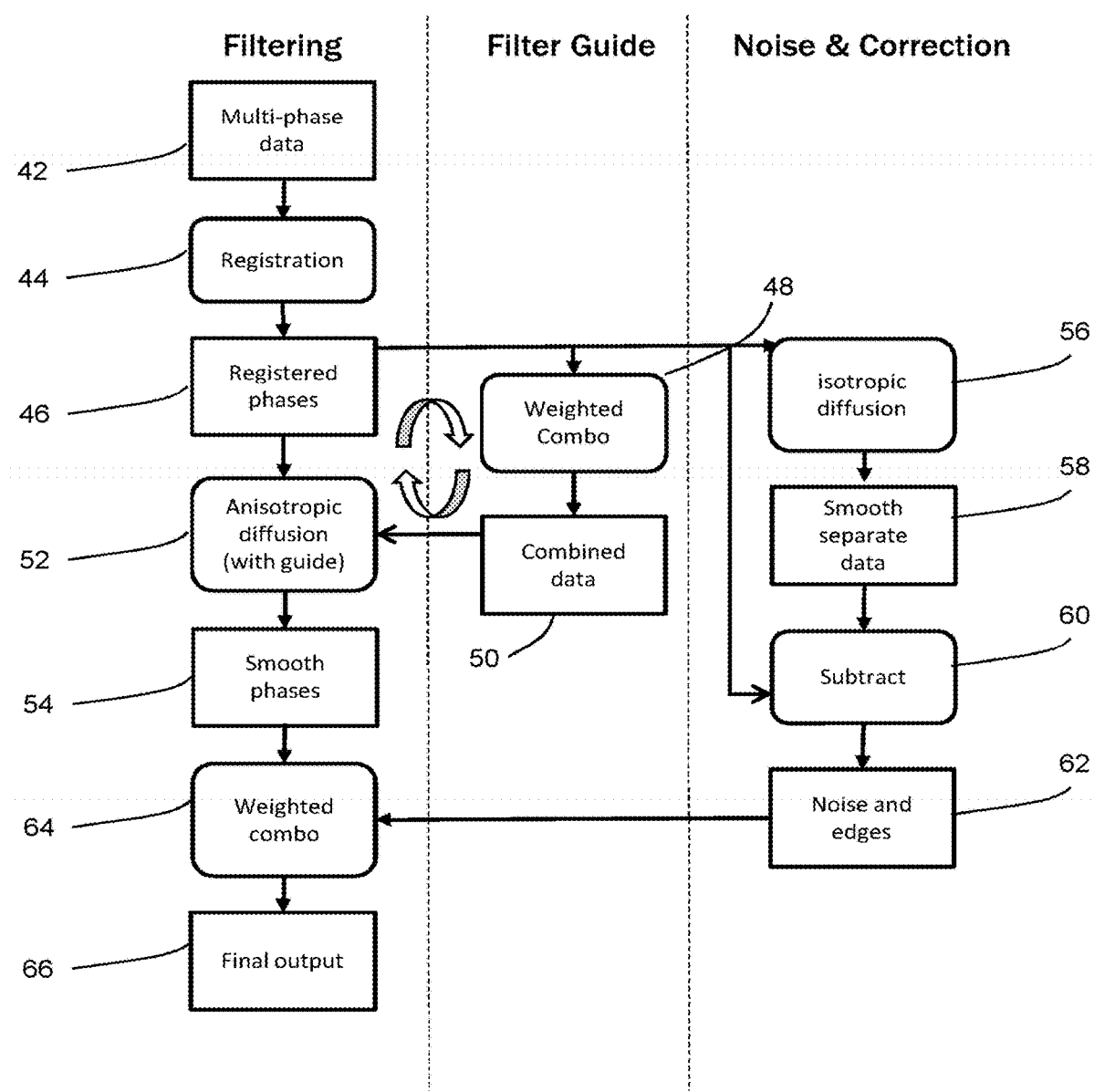
FIG. 2 is a flow-chart of an image filtering method in accordance with an embodiment.

FIG. 2 is a flowchart illustrating in overview a method for filtering imaging data sets in accordance with an embodiment. Each of the method steps can be considered as being in one of three parts of the method: a filtering part, a filter guide part and a noise and correction part. In the method of FIG. 2, as described in the following, the filter is an anisotropic filter applied to each separate that uses a secondary function, in this case, a guide based on gradient information derived from combining the data.

Figure 3:
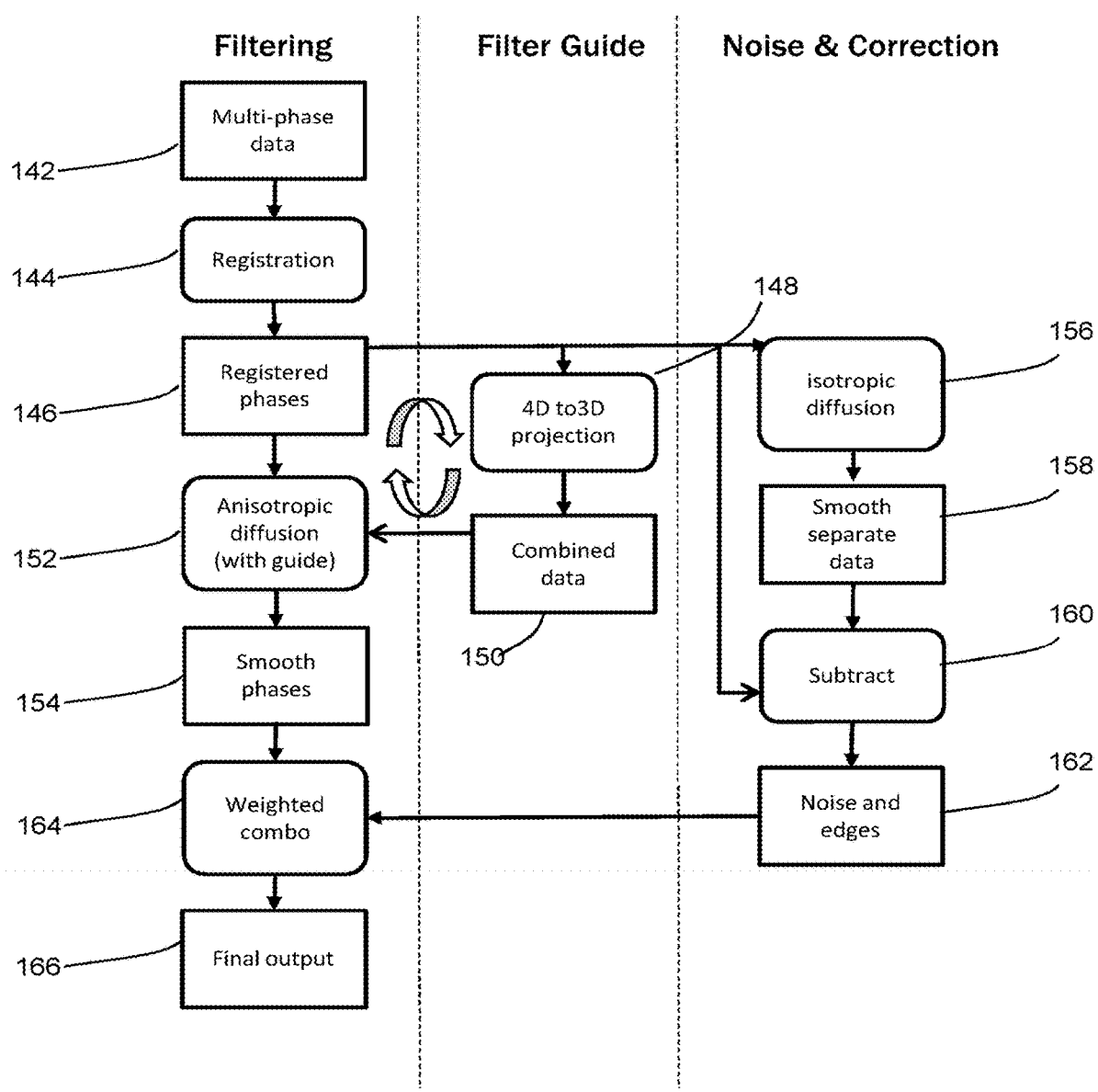
FIG. 3 is a flow-chart of an image filtering method in accordance with a further embodiment.

The steps depicted in FIG. 2 and in FIG. 3 are represented by either round or square shapes (rounded corners or square corners). The round shapes represent processing steps and the square shapes represents data steps, for example, steps where data is acquired, generated, outputted or otherwise obtained.

At step 42, as part of the filtering part of the method, a plurality of medical imaging data sets is acquired. Each data set of the plurality of imaging data sets corresponds to a respective different measurement period. The plurality of medical imaging data sets may therefore be referred to, collectively, as multi-phase data. Each set of the medical imaging data sets corresponds to a separate phase. The medical imaging data sets may also be referred to as the input data sets. In the present embodiment, each acquired medical imaging data sets comprises volumetric, spatial data. The medical imaging data thus provides a spatial representation of a volume being scanned during the scanning process.

In the present embodiment, the plurality of medical imaging data sets is acquired by operating the CT scanner 14 at respective different times. In the present embodiment, each imaging data set is a volumetric CT data set and may therefore be referred to as an input volume. In other embodiments, any suitable type of imaging data may be used.

At step 44, a registration process is performed, by registration circuitry 24, on the acquired medical imaging data sets to align the medical imaging data sets to provide a plurality of spatially registered data sets at step 46. The plurality of spatially registered data sets may also be referred to as registered phases. It will be understood that a number of known spatial alignment methods can be used at step 44.

In embodiments in which the medical imaging data sets are acquired in, or transformed to, a different representation that is not a spatial representation (for example, where the medical imaging data sets are represented in sinogram space) step 44 may either be omitted or the alignment process may align the data in accordance with this other representation.

Steps 48 and 50 of the method, performed by filter circuitry 26, are filter guide steps. As part of the method, a guide for a filter to be applied to each of the plurality of medical imaging data sets is generated. In the present embodiment, the guide is formed by, first combining the medical imaging data sets and using the combined data set to form the guide. It will be understood that other methods for combining data or for forming a guide may be performed and such methods are discussed with reference to FIGS. 3 to 7. The guide may be referred to as a gradient map or a guide map, depending on the embodiment being described.

In the present embodiment, at step 48, the set of registered data sets are combined, by the filter circuitry, to produce a combined data set at step 50. In the present embodiment, the registered data sets are combined by performing a weighted averaging, however it will be understood that other combining processes for combining the registered data sets may be used. The combining of data sets, which in the present embodiment is performed by a weighted averaging, provides a combined data set with less noise and better edge definition relative to each of the initial imaging data sets.

The weights used for combining are pre-determined. The weights may be selected such that imaging data sets with relatively better edge definition are weighted more in the averaging than imaging data sets with less defined edges. For example, a contrast scan may be expected to have better defined edges compared to a non-contrast scan and therefore the corresponding imaging data for the contrast scan may be weighted more in the combining process. In the present embodiment, gradient information is obtained from combined data set to provide the guide. The guide therefore provides more complete gradient information for the volume being scanned than would otherwise be provided by obtaining and using gradient information from a single phase. In addition, the combined data has less noise than the data set from the single phase. In some embodiment, the image data sets are combined using a projection process, for example, Maximum Intensity Projection.

The filter applied at step 52 is subject to a constraint and/or condition that a measure of the signal or a measured value of the signal is conserved. In the present embodiment, a measure of the density is conserved for the data set corresponding to each phase. Therefore, while data from different phases are combined to provide the combined data at step 48, it is the gradient information extracted from this combined data that is used for the filter (i.e. no density information is used from the combined data for the filter). By extracting only gradient information for the filter it is ensured that a measure of density for each data set is conserved and therefore that there is substantially no density leak between different phases.

By reducing density leak between different phases, any medical and functional information that is provided by the density of an image is retained. For scans using contrast agents, any information provided by the presence or absence of the contrast is preserved by the filtering. In other words, the filtering allows the sematic/structural information to be shared between phases. An example of semantic/structural information that is shared is that a particular area is an edge of a vessel. However, "absolute" information (for example, a parameter such as HU (Hounsfield unit) values themselves, in a small neighbourhood at least) is not shared.

By reducing density leak between different phases, multi-phase scans may be performed with a reduced dose. In further detail, the noise reduction may allow use of a reduced dose, and the density leakage constraint may allow a more powerful noise reduction.

The method provided in accordance with embodiments, may allow reduced dose multi-phase scans to be used while retaining a comparable image quality to higher dose scans. The density leakage constraint may allow a more effective noise reduction.

In the present embodiment, overall density of each of the plurality of imaging data sets is preserved by virtue of only using gradient information extracted from the combined data when applying the filter. It will be understood that the constraint may be implemented using different methods, for example, the constraint may be encoded in the filter parameters or an additional constraint term may be added to the filter.

At step 52, the anisotropic diffusion filter is applied to each of the spatially registered imaging data sets. The filter is applied to each data set separately such that for each imaging data set, a filtered data set is produced, at step 54. As the anisotropic diffusion filter acts to smooth the imaging data sets corresponding to the multiple time periods, the filtered data sets of step 54 may also be referred to as smooth phases.

The application of the anisotropic diffusion filter is an iterative process. In particular, the filter is applied over a number of time steps. Therefore, steps 46, 48, 50 and 52 are iteratively repeated until either a pre-determined number of times or until a pre-determined condition is met. For each iteration, the combined data and therefore the gradient information used for the anisotropic filter is updated.

While in the present embodiment, for each iteration, the combined data and therefore the gradient information used for the anisotropic filter is updated, it will be understood that in alternative embodiments, the guide may be kept constant throughout the iterations. While not updating the guide on every iteration may reduce the number of processing steps, a disadvantage of not updating may be that any initial noise is maintained in the guide and may not be smoothed out.

The combined data produced at step 48 provides the gradient information for the filter but does not provide density information. The filtering step may therefore not perfectly preserve edges and/or may remove too noise for the purpose of presentation to a medical professional. Therefore, the filtered data sets are adjusted via a further noise and correction process performed on the filtered data sets.

The steps of the noise and correction process are depicted in FIG. 2 as steps 56, 58, 60 and 62. These steps, performed by the filter circuitry 26, allow noise and edge information to be estimated from the individual data sets obtained at step 46 and then re-introduced into the filtered data sets.

As described in further detail in the following, the noise and correction process involves performing a smoothing process on the combined data of step 50. The original combined data is then subtracted from the smoothed combined data to provide a subtracted data set that provides an estimate of only noise and edge information.

In further detail, at step 56, an anisotropic diffusion filter is applied to each of the data sets from step 46 to provide smoothed, separate data sets at step 58. In contrast to step 52 in which gradient information from all phases is used for the filter, at step 56, such gradient information is not used for this filtering process. Therefore, step 56, of applying an anisotropic diffusion filter without a guide may be considered as equivalent to the step of applying an isotropic diffusion filter because the smoothing is applied equally in all directions and everywhere. By applying the smoothing without a guide, the noise and edge in each obtained data set is softened.

At step 60, performed by the filter circuitry 26, a subtraction process is performed using each smoothed data set, from step 58, and the corresponding, unsmoothed data set from step 46 to provide an estimate of noise and edges, at step 62. In some embodiments, the edge and noise information are separated by using texture of frequency analysis allowing edges to be recombined in full, with a separate weight for the noise. In such an embodiments separate noise and edge data sets are formed.

At step 64, performed by the filter circuitry 26, each individual filtered data set, also referred to as the smoothed phases, from step 54, is combined with the noise and edge information determined at step 62 to provide the output imaging data sets. At this step, noise is added back into the filtered data sets to provide an aesthetic effect. It has been found that a medical professional is more comfortable viewing and working with images that have some noise than smoothed images. In addition, adding the noise and edge information may increase sharpness of edges as, despite the anisotropic nature of the filtering process, some smoothing of edges may occur at previous steps.

At the final output stage, in the present embodiment, the output imaging data sets are rendered by the display circuitry 28 and displayed on display screen 16. It will be understood that in other embodiments, the output imaging data sets may be stored on memory 20 or provided to a further computing apparatus.

It will be understood that, in the embodiment described with reference to FIG. 2, the adjustments made to the filtered imaging data sets (the noise and correction steps 56, 58, 60 and 62) also satisfy the same density leakage constraint satisfied by the filtering step 52. In particular, the filter step 52 uses only gradient information from the combined data when applying a filter to the registered spatial imaging data sets. It will be understood that, in other implementations, the filter steps satisfy the density leak constraint but these further adjustment steps (noise and edge steps) do not satisfy the density leakage constraint. In such implementations, the applied filter at step 56 is applied to the combined data, rather than to separate phases data and therefore, by nature of the combination, density information may be shared between phases.

Further embodiments in which the adjustment to the filtered imaging data sets (the noise and correction steps) satisfy a density constraint between phases are described with reference to FIGS. 3, 4 and 5.

FIG. 3 is a flowchart of a method in accordance with embodiments. Filtering steps 142, 144, 146, 152, 154, 164 and 166 correspond substantially to steps 42, 44, 46, 52, 54, 64 and 66 that are described with reference to FIG. 2. In addition, noise and correction steps 156, 158, 160 and 162 correspond substantially to steps 56, 58, 60 and 62, respectively that are described with reference to the method of FIG. 2. In contrast to the method of FIG. 2, filter guide steps 148 and 150 replace filter guide steps 48 and 50.

In further detail, at step 148, a gradient image is determined using the spatially registered data sets. The gradient image is determined by projecting from a four dimensional space to a three dimensional space to produce combined data at step 150. In the present embodiment, a time-maximum intensity projection (time-MIP) is used, however, any suitable projection from four dimensions to three dimensions may be used. The time-MIP projection process involves determining gradients from each phase and combining the gradients by averaging. Other projections may be used, for example, AveIP projection. In the method of FIG. 3, gradient information from the gradient image derived via the 4D to 3D projection is used for the anisotropic diffusion filter at step 152.

While FIG. 3 describes noise and correction steps 156, 158, 160 and 162 that correspond to previously described steps 56, 68, 60 and 62 respectively, it will be understood that in other embodiments, the filtered imaging data sets are adjusted at using noise and edge information that is obtained only from the particular phase that is being smoothed rather than from a combined data set. For example, the method may include a step in which the non-filtered version of the registered data set is subtracted from the filtered data set to provide edge and noise information for the specific phase. The noise and edge information for each phase is then added back to the filtered data set for the corresponding phase. The noise and edge information may be added back in with some parameterised weight.

The degree of smoothing may be applied and controlled using different methods. A first non-limiting example, is to change the number of iterations the diffusion process runs for. This will have an effect on strength of the smoothing effects are and how large the smoothing effects are. As the number of iterations increases the affected area of the smoothing also increases. A second, non-limiting example, is to use a parameterised weight to control the amount of smoothing. Using the parameterised weighting allows running of the smoothing process for more iterations (thereby increasing effect size) without having to also increase the strength of smoothing.

In further embodiments, described in further detail with reference to FIGS. 4 and 5, the determination of the guide for the filter (steps 48 and 50) is performed using an AI model. In particular, a trained model, in this embodiment, a trained convolutional neural network (CNN) is used to predict a guide map for use by the filter (rather than, the weighted average or projection described with reference to FIGS. 2 and 3). The guide map provides a guide for the diffusion filter. The CNN may predict a guide for the anisotropic diffusion filter by processing input data sets. In some embodiments, the CNN may be trained to provide a guide based on information alternatively or in addition to the gradient information. For example, the CNN may be trained to detect other features that are representative or indicative of edges or may be trained to detect other features, for example, anatomical features.

It will be understood that the guide map performs a similar role in this embodiment as the gradient map described with reference to FIGS. 2 and 3. In some embodiments, the guide map corresponds to a gradient map.

Figure 4:
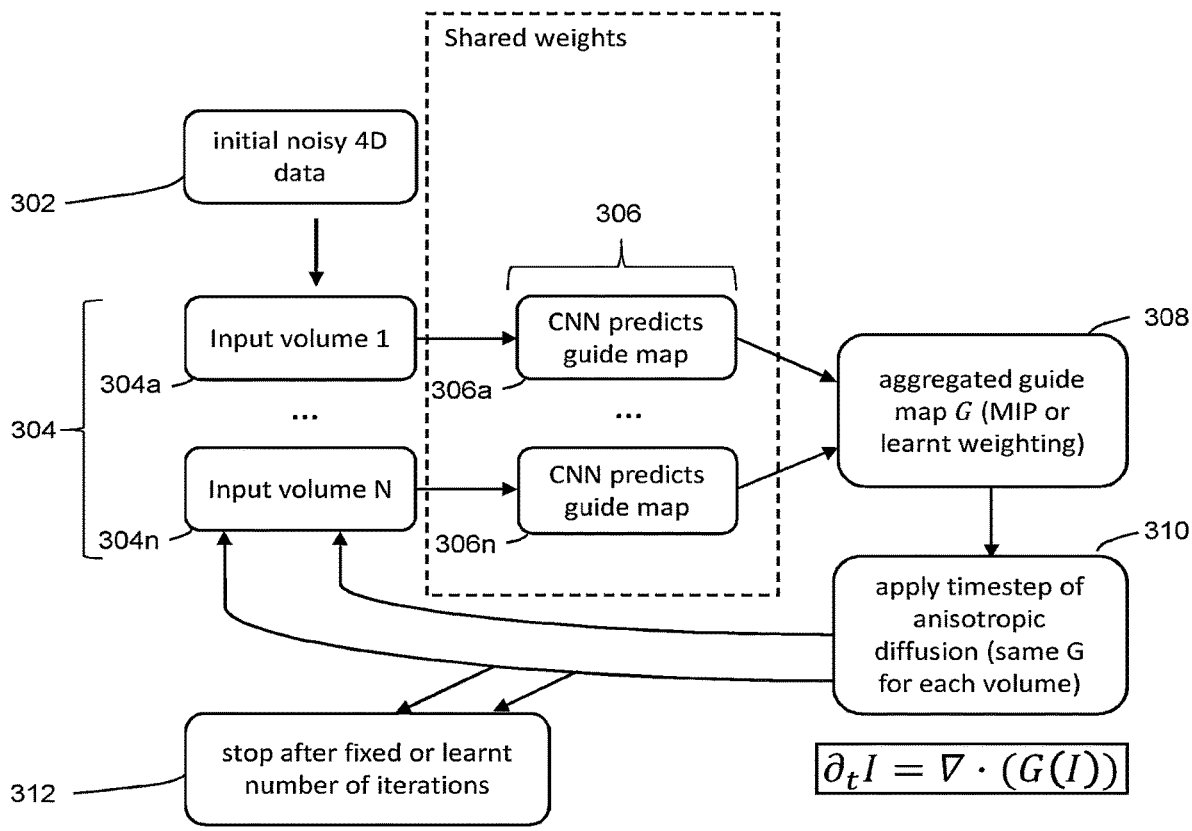
FIG. 4 is a flow-chart of an image filtering method using a neural network and a filter, in accordance with an embodiment.

It will be understood that while FIG. 3 and FIG. 4 describes using a trained CNN, in other embodiments, different models trained using machine learning processes can be used.

FIG. 4 shows a flowchart describing a method using a CNN in combination with a filter, in accordance with a first embodiment. FIG. 5 shows a flowchart describing a method using a CNN in combination with a filter, in accordance with a second embodiment.

For the method of FIG. 4, a preliminary step of providing a trained convolutional neural network is performed. This may involve training the network or otherwise obtaining trained parameters for the network. The training data used for the training process is high quality and denoised training data.

At step 302, initial four-dimensional imaging data (comprising three spatial dimensions and a time dimension) is provided. At the initial step, these four-dimensional data correspond to the acquired plurality of medical imaging data set for each of N phases $304a, \ldots, 304n$. Each data set may also be referred to as an input volume.

At the second step 306, the imaging data set for each phase is input to a trained convolutional neural network. In the embodiment of FIG. 4, at step 306, each input data set if provided to a convolutional neural network trained to output a separate guide map. The convolutional neural network operating on each data set has a common set of trained parameters, also referred to as shared weights that are determined through the training network.

In further detail, a first imaging data set (input volume 1) is obtained at step 304a and, at step 306a, input to the convolutional neural network characterised by the shared weights. The convolutional neural network then outputs a first predicted guide map. Likewise, at step 304n, an nth imaging data set is obtained and is, at step 306n, input to the convolutional neural network characterised by the shared weights to output an $n^{th}$ guide map. It will be understood, that although only the process for the first and $n^{th}$ imaging data sets is described, the same process is performed on the $2^{nd}$ to $(n-1)^{th}$ imaging data sets, such that n, separate, guide maps are generated from n input volumes.

At step 308, the generated guide maps are combined, in the present embodiment, through aggregation, to generate an aggregated guide map, referred to by the symbol G. Steps 306 and 308 together are considered as corresponding to filter guide steps 48 and 50 of FIG. 2, in that combined data is provided using a combining process (in this case n individual guide maps are predicted and then aggregated to provide gradient information for the filter in the form of an aggregated guide map).

The guide may be aggregated using a number of different combining methods. As a first non-limiting example, the guide maps may be aggregated over multiple cases using a MIP projection algorithm using max pooling. Alternatively, the maps may be summed, for example, by using a weighted sum. The parameters of the weighted sum or averaging (the weights) may be pre-determined or also determined during a training process.

As the diffusion equation used for the filter is differentiable, there can be back propagation through the diffusion equation and the CNN. A neural network is typically trained using a process called back-propagation, in which an error is calculated using the output of the neural network, then the gradient of that error is passed backwards through the network until it reaches the trainable weights. The weights are then adjusted using the gradient to minimize error. This is an iterative optimization process.

In this embodiment, an error cannot be computed directly on the output of the network because there is no best guide map, therefore there a comparison between the output of the network and a best guide map to determine an error cannot be performed. It is possible to train the neural network to predict a gradient map.

As a non-limiting example, the error is computed as follows. Artificial noise is added to the smoothed volume to obtain the input volume. An error is then computed on the smoothed volume because it is known what the smooth volume should look like. For back-propagation of this error to occur all the preceding computations must be differentiable. The diffusion process is naturally differentiable so is convenient to use with back-propagation, allowing the network to be trained efficiently.

At step 310, a single time step of the anisotropic filter is applied to each imaging data set (the first to the nth imaging data set) to evolve the imaging data to produce a corresponding updated imaging data set. For a given iteration, each application of the filter uses the aggregated guide map determined during this iteration.

In further detail, the anisotropic filter is defined by the mathematical function:

$$\partial_t I = \nabla \cdot (G(I))$$

where I represents the image data being filtered and G represents the aggregated guide (the same G is used for each volume) being used by the filter. $\partial_t$ represents the time differential operator and $\nabla$ represent the spatial differential operator.

Following the application of a timestep of the anisotropic diffusion filter (using the same aggregated guide for each volume) the output of this single timestep (the updated input volume) is then input back into the CNN (the method returns to step 304) for the next iteration. For each iteration, a new aggregated guide map is determined based on the output from applying the trained CNN to the input volume.

The above process is repeated until, at step 312, a pre-determined number of iterations have been performed. The number of iterations performed and thus number of timesteps applied for the anisotropic diffusion filter is defined by a parameter. In some embodiments, that parameter is a pre-determined parameter. In other embodiments, the parameter is a learnt parameter using a machine learning technique. In some embodiments, the parameter is provided by a user.

Figure 5:
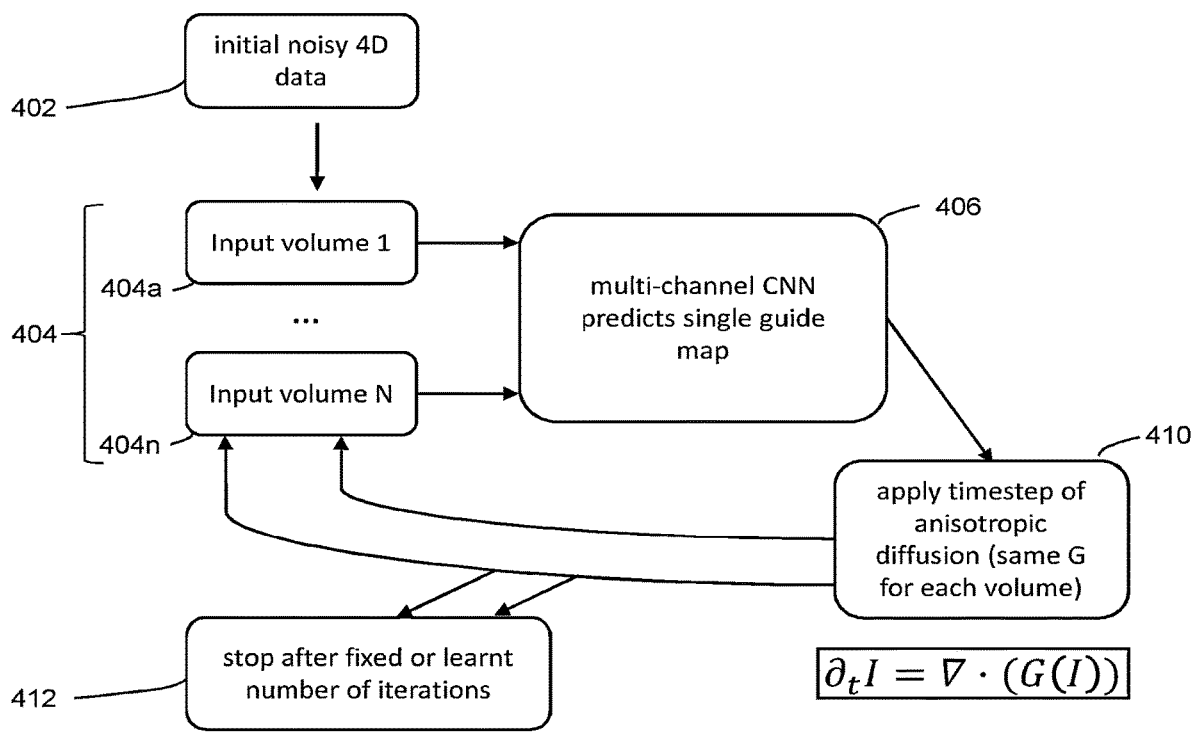
FIG. 5 is a flow-chart of an image filtering method using a neural network and a filter, in accordance with a further embodiment.

FIG. 5 depicts a method using a CNN related to the method depicted in FIG. 3. The method of FIG. 5 has a number of steps in common with the method of FIG. 4 (in particular, steps 402, 404, 410 and 412 correspond to steps 302, 304, 310 and 312). However, in place of a trained CNN being applied to each input volume separately and combining the output of the CNN to produce a guide map (steps 306 and 308), a trained multi-channel CNN predicts a single guide map at step 406. The single gradient map formed by the multi-channel CNN provides the single gradient map for the filter step 410.

In the embodiments depicted in FIGS. 4 and 5, a guide map for the diffusion process is described as being determined by one or more CNNs. It will be understood that other parameters used in the process may be determined by neural networks or other machine learning techniques. By way of non-limiting examples, coefficients for the diffusion equation or the number of iterations required by the filter may be determined. It will be further understood that other learning algorithms and other models may be suitable.

Figure 6:
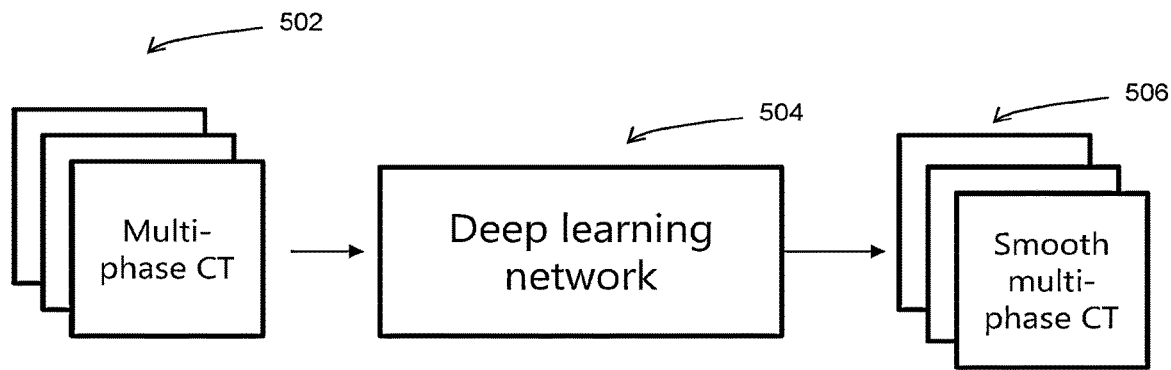
FIG. 6 is an overview of an image filtering method using a deep learning network in accordance with an embodiment.

FIG. 6 depicts a further method, in overview of a method of filtering images using a deep learning network. In contrast to the methods described with reference to FIGS. 2, 3, 4 and 5, no anisotropic diffusion filter is used in this method. Instead, the deep learning network is trained to perform the filtering process on the plurality of input medical imaging data sets from different, respective periods and output a corresponding plurality of filtered data sets. The constraint of reducing density leak between different phases is satisfied by this embodiment by including a loss or penalty term when training the network. The loss term penalises differences in a measure of density or intensity between the output images and the input images. The density constraint or condition can therefore be considered as encoded in the network parameters.

FIG. 6 depicts the trained deep learning network 504, in use. The deep learning network 504 is, for example, a general adversarial network (GAN), operating on multi-phase medical imaging data 502, in the present embodiment CT scan data. The deep learning network is trained to produce smooth, multi-phase, filtered CT scan data 506.

Figure 7:
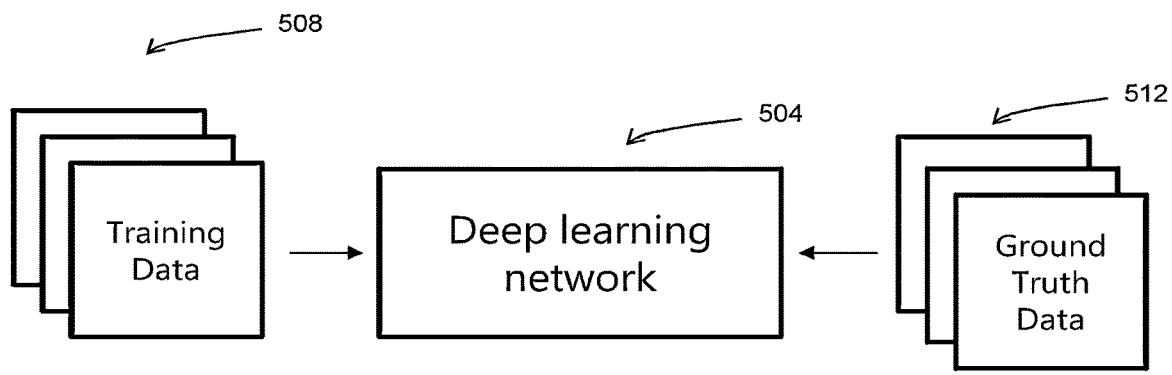
FIG. 7 is a flow-chart illustrating a training method for training the deep learning network.

FIG. 7 depicts a training method for training the deep learning network 506. To train the deep learning network, training data 508 is provided to the deep learning network 506. The training data 508 is multi-phase medical imaging data 506. In the present embodiment, the training data is noisy, simulated data. In some embodiments, the input data may be acquired by combining good quality image with simulated noise. To train the GAN, high resolution medical imaging data is used as ground truth data 512.

In other embodiments, a method of obtaining good quality data is to perform a further filtering method that, for example, would not be suitable for the purposes of the present scanning process. For example, the further filtering method may use a large amount of resources or more data than the filtering method in accordance with embodiments.

In one embodiment, the training method penalises differences between the total density of an input image and the total density of the corresponding output image such that the filter applied by the GAN satisfies the density constraint. In further detail, a penalty function or loss term or loss function is applied during a training process. The penalty function or loss term may be such that, for example, any difference between a global intensity of an output phase is compared to ground truth data. In a further example, the penalty function or loss term may penalise a difference between intensity of an output phase when compared to ground truth data, as computed at multiple local scales (for example using an average or sum convolution operation).

In a further embodiment, a sum-pooling kernel is used to evaluate the density at multiple scale levels. Differences in the density of the input and output at different scales levels will incur a penalty during the training, by virtue of the loss term. By training the deep learning network with the penalty or loss term, a density constraint for each input image is encoded in the network such that density leakage between phases does not occur.

The deep learning network 504 is characterised by a number of trained model parameters. The value of these trained model parameters determine how an input volume is filtered to produce an output data set (smooth CT image). The model parameters are therefore trained such that substantially no density leakage occurs between phases when the deep learning network 504 operates on the input data. While a GAN is described, other deep learning networks may be used. For example, an encoder/decoder or residual network may be used.

Figure 8:
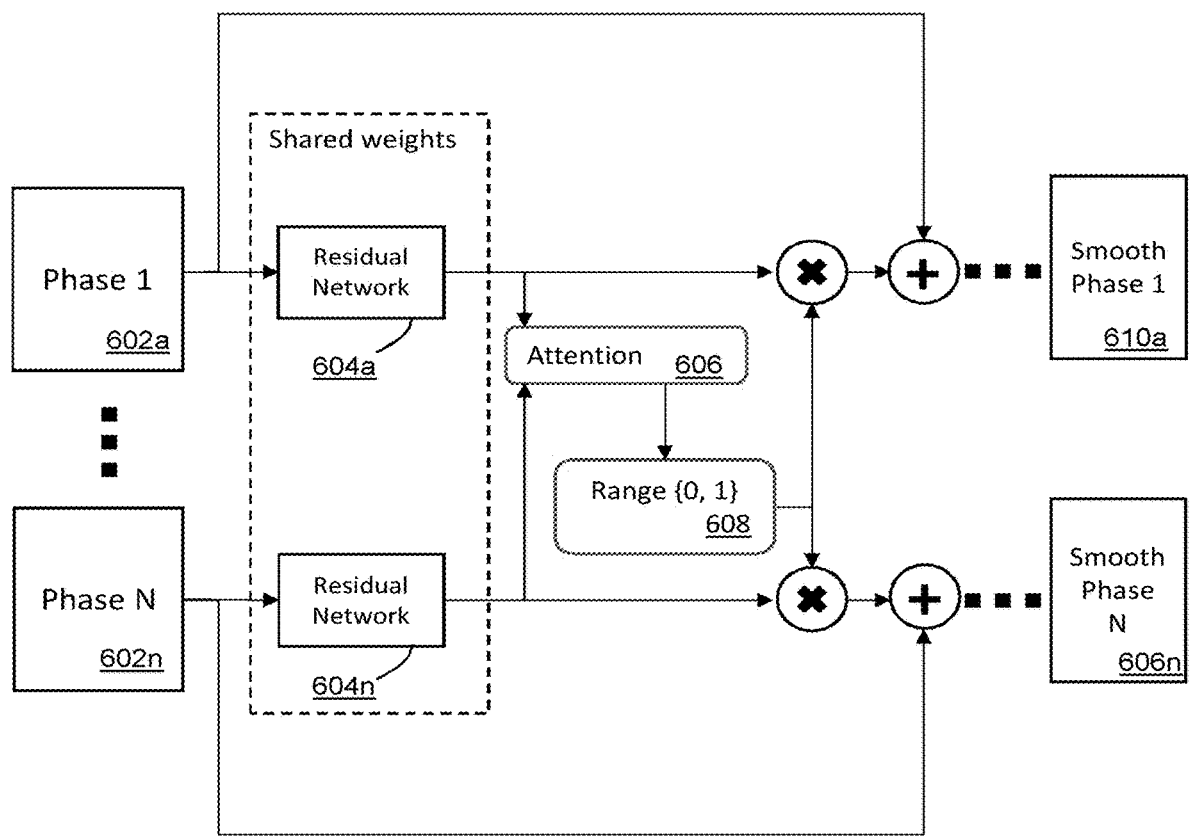
FIG. 8 is a flow-chart of an image filtering method using an attention mechanism.

FIG. 8 depicts a method in accordance with a further embodiment. In the embodiment of FIG. 8, information is shared between phases, by an attention mechanism 606. A set of n input medical imaging data sets (602a, ..., 602n)

are input to a set of n filtering networks also referred to as residual networks (604a, . . . , 604n) and a set of n, filtered, medical imaging data sets (610a, . . . , 610n) are output. The set of n filtering networks are trained and use shared weights.

In contrast to the previously described neural network methods, the method of FIG. 8 has an attention mechanism 606 allowing the neural network to focus on particular features of the input images. An attention mechanism or module uses information from all phases to determine a common attention map. The common attention map is then used to restrict application of smoothing to each phase. The attention mechanism allows spatially adaptive filtering of a particular target phase according to the contents of all phases. In this way at least some information from the other phases are used when filtering a particular phase.

The general structure of the network depicted in FIG. 8 is a residual network. This is a network that uses skip layers so that the network only learn the difference between an input and an output instead of having to reproduce the input data. In the example of FIG. 8, the network is configured to only learn changes that need to be made to an input image in order to make it smoother. This filtering part of the network only has access to data from each individual phase. The filtering part of the network may use shared weights to reduce the number of parameters that require trained.

The attention mechanism receives data sets from all phases (602a . . . 602n) as input. The attention mechanism may also receive the outputs of the residual networks (604a . . . 604n) as input.

An attention map 606 is generated which will be multiplied with the output residual. The result of the multiplication is added to the input data and this will be the final output of the algorithm. Effectively, this means the attention map 606 is deciding where and to what extent the smoothing will occur.

To prevent the attention map 606 leaking density between the phases the values of the attention map 606 are limited to be in the range {0, 1}, as represented by numeral 608 of FIG. 8. This means that the attention map is only able to decide how much of the residual is applied to the input. Since each residual network only sees a single phase, density is not leaked between phases.

In the above described embodiments, methods of filtering medical images from multiple, different time periods are described. When comparing the filtered image from a single phase with the input image from a single phase, a number of differences are observed. For example, the level of noise is reduced in the filtered image. The describe method intends to not smooth meaningful content, for example, edges. The described method therefore does not smooth or change the edge, however, a reduction in noise make the edges appear more apparent.

The improvement in processed images may also be assessed by comparing the filtered images with images obtained using other, known, smoothing processes. With reference to the output of other, known, smoothing processes, the edge definition may be improved.

In the above described embodiments, a constraint or condition is described which preserves a measure of intensity between phases. For embodiments using CT scan data, the measure of intensity corresponds to a measure of density, for example, radio density. It will be understood that density and/or intensity may be measured over a group of voxels, for example, over a local region of the scan data or globally over the region of the scan data. Furthermore, in further embodiments, for scans in which contrast is used for one phase, the method may act such that substantially no contrast information is transferred between phases.

For example, in the context of CT scans, density, also referred to as radio density, of a scanned tissue is proportional to the attenuation of x-ray which pass through the tissue.

For example, density may be measured in Hounsfield Units or other appropriate units. For other types of scan, the constraint may be applied to a measure of intensity of a measured signal or a quantity derived from the scan data. As a non-limiting example, the detected intensity of the scan may be proportional to, for example, the level of a signal reflected, transmitted, attenuated or scattered during the scan. As a further non-limiting example, the constraint may be a measure of density/intensity that is derived from a region of an obtained image/volume, for example, a sub-region of an image may have a particular value of density or intensity. In some contexts, intensity may refer to a property of the image data itself (for example, related to brightness or darkness of the image).

Certain embodiments provide a medical imaging method comprising: acquiring a plurality of sets of medical imaging data (typically, CT data) of a region of a subject, each set of data corresponding to a respective different measurement period; performing a registration procedure to spatially align the plurality of sets of medical imaging data (typically, CT data); applying a filter to the spatially aligned medical imaging data sets (typically CT data) to produce a set of filtered medical imaging data sets corresponding to the different measurement periods, wherein the applying of the filter is such that, for each of the medical imaging data sets, the filtering uses at least some information from the other medical imaging data sets acquired at the different time periods.

The applying of the filter may comprise applying a 4D (3 spatial dimensions and time) filter. The filter may comprise an anisotropic diffusion filter. The information from the data sets that is used by the filter may comprise gradient information. The method may comprise obtaining combined information (optionally gradient information) from all of the data sets, and applying the filter to each of the data sets individually using the combined information. The applying of the filter may comprise applying at least one constraint or condition and the constraint or condition comprises preserving overall (e.g. average or total) density or intensity values for each data set.

The method may comprise obtaining a combined data set from the plurality of data sets (optionally by applying a further filter to the combined data sets) and using the combined data set, or information (e.g. edge and/or noise information) obtained from the combined data set when applying the filter to the data sets.

The method may comprise adjusting the filtered data sets using said information from the combined data set (e.g. edge and/or noise information), after the applying of the filter.

The region of the subject may comprise an anatomical feature of interest. The medical imaging data sets may comprise at least one contrast medical imaging data set and at least one non-contrast medical imaging data set. The medical imaging data sets may comprise at least one data set acquired prior to a medical treatment and at least one data set acquired after said medical treatment. The different measurement periods may comprise different time points or different, non-overlapping periods of time. The filtered data sets may have reduced noise and/or improved edge definition compared to the data sets before applying of the filter.

Certain embodiments provide a medical imaging method comprising: acquiring volumetric imaging data from a plurality of time points; applying some form of spatial alignment across the time points; apply filtering informed by 4D information but such that overall density is preserved for each individual volumetric imaging data; outputting the plurality of independent volumes. The medical imaging method may be applied in spatial or sinogram space.

The filtering may be performed by a neural network which has an explicit constraint to reduce transfer of density information across phases. The constraint may be applied during training via a loss term which could be, for example, a difference between global intensity of output phase compared to ground truth (could use average or sum operation) and/or a difference between intensity of output phase compared to ground truth computed at potentially multiple local scales (for example using average or sum convolution operation), The constraint may be applied via structural components comprising: each phase is processed individually through the network or an attention module which uses all phases to determine a common attention map which is used to restrict the application of smoothing to each phase.

The volumes may be reconstructed to volumetric image space and anisotropic diffusion is used to preserve overall density. The gradient image may be a 3D projection of the 4D inputs, for example, a projection along the time axis (e.g. MIP, AveIP) or a weighted combination of each of the time points. The edges and potentially image noise of the individual time points may be added back into the filtered image with some parameterised weight. Neural networks may be used to calculate the weighted gradient map used during the anisotropic diffusion process. Neural networks may be used to calculate the diffusion coefficient values used during the anisotropic diffusion process.

In the above-described embodiments, neural networks are described. However, it will be understood that in other embodiments, other filter models trained using suitable machine learning processes can be used. For example, suitable machine learning processes may be used to obtain a trained filter model based on classification and/or regression techniques.

In the above-described embodiments, it is in intended that density information is never shared between phases such that there is no density leak between phases. In some embodiments, for example, in embodiments using a trained filter model, a small amount of density leak may occur, unintentionally, however, it will be understood that the amount of density leakage will be minimal. In particular, the density leakage will be low enough that the clinical interpretation of the image is unaffected. In practice, a clinical evaluation is performed to determine if any unintentional leakage was acceptable. Such an evaluation would be context dependent. In some embodiments, a value representative of density leakage is measured, for example, by processing the filtered images. The measured value may be compared to a threshold value to ensure that any unintentional leakage is kept below a minimum value.

Whilst particular circuitries have been described herein, in alternative embodiments functionality of one or more of these circuitries can be provided by a single processing resource or other component, or functionality provided by a single circuitry can be provided by two or more processing resources or other components in combination. Reference to a single circuitry encompasses multiple components providing the functionality of that circuitry, whether or not such components are remote from one another, and reference to multiple circuitries encompasses a single component providing the functionality of those circuitries.

Whilst certain embodiments have been described, these embodiments have been presented by way of example only, and are not intended to limit the scope of the invention. Indeed the novel methods and systems described herein may be embodied in a variety of other forms; furthermore, various omissions, substitutions and changes in the form of the methods and systems described herein may be made without departing from the spirit of the invention. The accompanying claims and their equivalents are intended to cover such forms and modifications as would fall within the scope of the invention.

The invention claimed is:

1. An apparatus comprising:
processing circuitry configured to:
acquire a plurality of sets of medical imaging data of a region of a subject, each set of data corresponding to a respective different measurement period; and
apply a filter to the plurality of medical imaging data sets to produce a plurality of filtered medical imaging data sets corresponding to the different measurement periods, the filter being applied to each medical imaging data set to produce a corresponding filtered medical imaging data set for each measurement period, wherein
applying of the filter is such that, for each of the medical imaging data sets, the filtering uses at least some information from the other medical imaging data sets acquired at the different measurement periods, and
applying of the filter comprises applying at least one constraint or condition and the constraint or condition comprises preserving at least one measure of intensity for each medical imaging data set for each respective measurement period.

2. The apparatus according to claim 1, wherein the medical imaging data set comprises CT scan data and wherein the at least one measure of intensity comprises at least one measure of density.

3. The apparatus according to claim 1, wherein the at least some information from the other medical imaging data sets used during the filtering comprises gradient information and/or edge information.

4. The apparatus according to claim 1, wherein the filter comprises a four dimensional filter wherein the four dimensions comprise three spatial dimensions and a time dimension and/or wherein the filter comprises an anisotropic filter.

5. The apparatus according to claim 1, wherein the filter comprises one or more trained multi-layer neural networks or other trained model.

6. The apparatus according to claim 1, wherein the processing circuitry is further configured to perform a registration procedure to spatially align the plurality of sets of medical imaging data and wherein the filter is applied to the spatially aligned medical imaging data sets.

7. The apparatus according to claim 1, wherein the processing circuitry is further configured to obtain combined data from at least some of the plurality of data sets and wherein applying the filter to each of the plurality of data sets comprises using the combined data and/or information obtained from the combined data.

8. The apparatus according to claim 7, wherein obtaining the combined data comprises performing a combining process on the plurality of medical imaging data sets, wherein the combining process is characterised by one or more weighting parameters.

9. The apparatus according to claim 8, wherein performing the combining process comprises performing at least one of: an averaging process; a summing process; at least one further filtering step; a projection from a higher dimensional representation to a lower dimensional representation; or applying at least one trained model and/or other function associated with a machine learning process.

10. The apparatus according to claim 7, wherein the processing circuitry is further configured to adjust the filtered data sets using noise or edge information obtained from the combined data set after the applying of the filter.

11. The apparatus according to claim 1, wherein the at least some information comprises or is comprised in a further function or mapping, wherein the further function or mapping is representative or at least indicative of at least one of: anisotropy and/or features and/or edges of the volume being scanned.

12. The apparatus according to claim 1, wherein the filter is characterised by at least one parameter and wherein the at least one parameter and/or the at least some of the information used by the filter is determined as part of a machine learning process.

13. The apparatus according to claim 1, wherein the applying of the filter comprises an iterative process comprising:
at least a first application to update each of the medical imaging data sets based on the at least some information from the plurality of medical imaging data sets acquired at the different measurement periods and a second application of the filter to the updated image data sets using at least some information from the other updated medical imaging data sets corresponding to the different measurement periods.

14. The apparatus according to claim 1, wherein the at least one preserved measure of intensity for each set of medical imaging data comprises at least one of:
average intensity, total intensity, a measure of intensity determined using a moving window, or one or more measures of intensity at one or more scales.

15. The apparatus according to claim 1, wherein the filter comprises a filter function and/or mapping, and wherein at least one of a), b), c), d) or e) occurs:
a) the constraint and/or condition is encoded in or added to the filter function and/or mapping;
b) the filter function and/or mapping is characterised by one or more filter parameters and the one or more filter parameters of the filter function and/or mapping are pre-determined, and wherein the one or more pre-determined filter parameters encode or characterise the at least one constraint or condition;
c) the filter function and/or mapping is characterised by one or more filter parameters and the one or more filter parameters and/or mapping are pre-determined from a training process performed on training data, wherein the training process comprises penalizing differences between a measure of intensity in an input imaging data and a measure of intensity in an output imaging data;
d) the filter function and/or mapping is characterised by one or more filter parameters and wherein the processing circuitry is further configured to obtain one or more filter parameters by applying a machine learning process to a plurality of training data sets comprising medical image data.

16. The apparatus according to claim 1, wherein at least one of a), b), c), d) or e) occurs:
a) the region of the subject comprises an anatomical feature of interest;
b) the medical imaging data sets comprise at least one contrast medical imaging data set and at least one non-contrast medical imaging data set;
c) the medical imaging data sets comprise at least one data set acquired prior to a medical treatment and at least one data set acquired after said medical treatment;
d) the different measurement periods comprise different time points or different, non-overlapping periods of time;
e) the filtered data sets have reduced noise and/or improved edge definition compared to the data sets before applying of the filter.

17. The apparatus according to claim 1, wherein
the medical imaging data set comprises CT scan data,
the at least one measure of intensity comprises at least one measure of density,
the at least some information from the other medical imaging data sets used during the filtering comprises gradient information, and
the filter comprises one or more trained multi-layer neural networks or other trained model.

18. The apparatus according to claim 1, wherein
the processing circuitry is further configured to
obtain combined data from at least some of the plurality of data sets, and
extract gradient information or edge information from the combined data, and
applying of the filter comprises using the extracted gradient information or edge information from the combined data.

19. A medical imaging method comprising:
acquiring a plurality of sets of medical imaging data of a region of a subject, each set of data corresponding to a respective different measurement period;
applying a filter to the plurality of medical imaging data sets to produce a plurality of filtered medical imaging data sets corresponding to the different measurement periods, the filter being applied to each medical imaging data set to produce a corresponding filtered medical imaging data set for each measurement period, wherein
the applying of the filter is such that, for each of the medical imaging data sets, the filtering uses at least some information from the other medical imaging data sets acquired at the different measurement periods, and
the applying of the filter comprises applying at least one constraint or condition and the constraint or condition comprises preserving at least one measure of intensity for each medical imaging data set for each respective measurement period.

20. A system comprising:
processing circuitry configured to train a filter for filtering medical images, wherein the filter is characterized by one or more filter parameters, by:
obtaining a plurality of sets of medical image training data of a region of a subject; and
performing a machine learning process on the plurality of sets of medical image training data to determine values for the one or more filter parameters thereby to obtain a trained filter,
wherein the trained filter is such that filtering a plurality of sets of medical imaging data of a region of a subject, each set of data corresponding to a respective different measurement period and the trained filter being applied to each medical imaging data set to produce a corresponding filtered medical imaging data set for each measurement period, using the trained filter, uses at least some information from the other medical imaging data sets acquired at the different measurement periods and comprises applying at least one constraint or condition and the constraint or condition comprises preserving at least one measure of intensity for each medical imaging data set for each respective measurement period.

21. A method for training a filter for filtering medical images, wherein the filter is characterized by one or more filter parameters, the method comprising:
  obtaining a plurality of sets of medical image training data of a region of a subject;
  performing a machine learning process on the plurality of sets of medical image training data to determine values for the one or more filter parameters thereby to obtain a trained filter,
  wherein the trained filter is such that filtering a plurality of sets of medical imaging data of a region of a subject, each set of data corresponding to a respective different measurement period and the trained filter being applied to each medical imaging data set to produce a corresponding filtered medical imaging data set for each measurement period, using the trained filter, uses at least some information from the other medical imaging data sets acquired at the different measurement periods and comprises applying at least one constraint or condition and the constraint or condition comprises preserving at least one measure of intensity for each medical imaging data set for each respective measurement period.

22. A non-transitory computer-readable storage medium comprising computer-readable instructions that are executable to:
  acquire a plurality of sets of medical imaging data of a region of a subject, each set of data corresponding to a respective different measurement period;
  apply a filter to the plurality of medical imaging data sets to produce a plurality of filtered medical imaging data sets corresponding to the different measurement periods, the filter being applied to each medical imaging data set to produce a corresponding filtered medical imaging data set for each measurement period, wherein
  the applying of the filter is such that, for each of the medical imaging data sets, the filtering uses at least some information from the other medical imaging data sets acquired at the different measurement periods, and
  the applying of the filter comprises applying at least one constraint or condition and the constraint or condition comprises preserving at least one measure of intensity for each medical imaging data set for each respective measurement period.

* * * * *